United States Patent [19]

Schonberger

[11] Patent Number: 4,482,414
[45] Date of Patent: Nov. 13, 1984

[54] FOAM-FILLABLE ENCLOSURE

[76] Inventor: Milton Schonberger, One Century Tower, Ft. Lee, N.J. 07024

[21] Appl. No.: 547,247

[22] Filed: Oct. 31, 1983

[51] Int. Cl.³ .................... B32B 1/04; B32B 1/06; B32B 3/18
[52] U.S. Cl. ............................. 156/79; 156/90; 156/310; 156/313; 206/524.1; 428/71; 428/76; 428/157; 428/194; 428/313.3; 428/321.5
[58] Field of Search ............. 206/524.1; 428/35, 68, 428/71, 76, 157, 166, 192, 194, 313.3, 313.5, 317.5, 321.5; 156/79, 90, 310, 313

[56] References Cited

U.S. PATENT DOCUMENTS

| | | | |
|---|---|---|---|
| 3,048,169 | 8/1962 | Pierce | 264/222 |
| 3,294,602 | 12/1966 | Francis et al. | 428/316.6 |
| 3,415,243 | 12/1968 | Sheldon | 128/90 |
| 3,423,489 | 1/1969 | Arens et al. | 264/4 |
| 3,563,234 | 2/1971 | Umstead | 264/222 |
| 3,676,288 | 7/1972 | Hoyle | 428/283 |
| 3,863,758 | 2/1975 | Connelly | 428/194 |
| 4,060,075 | 11/1977 | Blomer et al. | 128/90 |
| 4,272,898 | 6/1981 | Tansill | 428/376 |
| 4,273,827 | 6/1981 | Sweeney et al. | 428/316.6 |

FOREIGN PATENT DOCUMENTS 2267082 11/1975 France .

Primary Examiner—William J. Van Balen
Attorney, Agent, or Firm—Ostrolenk, Faber, Gerb & Soffen

[57] ABSTRACT

An enclosure for having foam generated and contained therein is defined between two layers of flexible thermoplastic material, which are edge sealed to define an enclosed unit. One inwardly facing surface of one layer is coated with a first foam generating agent, such as crystals, and the opposite, inwardly facing surface of the other layer is coated with capsules of another foam forming agent, wherein the capsules prevent mixing of the two agents for generating foam. Upon subsequent rupture of the capsules, the foam generating agents mix, react and generate foam in the enclosure. An additional layer may be disposed between the two exterior layers. Both surfaces of the additional layer also carry one of the foam forming agents, whereby two enclosures are defined, one over the other, each for generating and containing foam. In forming the enclosed unit, each layer is separately coated with its respective foam forming agent and thereafter the layers are secured together to define the enclosure.

20 Claims, 6 Drawing Figures

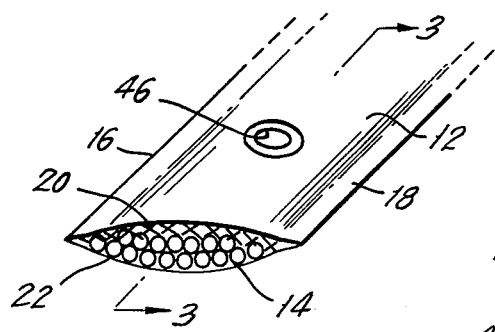
FIG. 1.
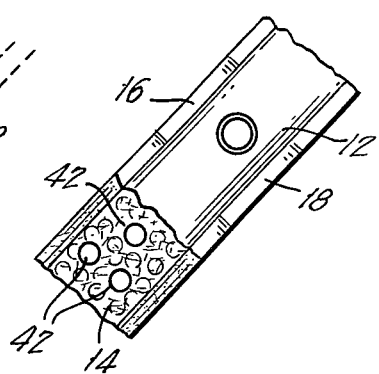
FIG. 2.
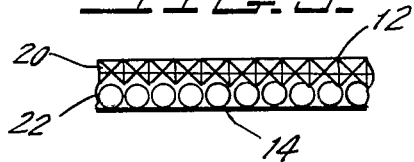
FIG. 3.
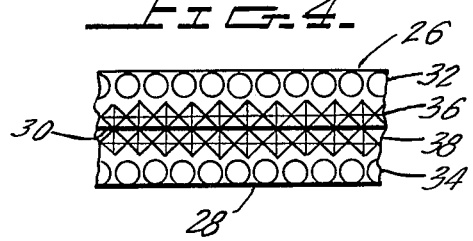
FIG. 4.
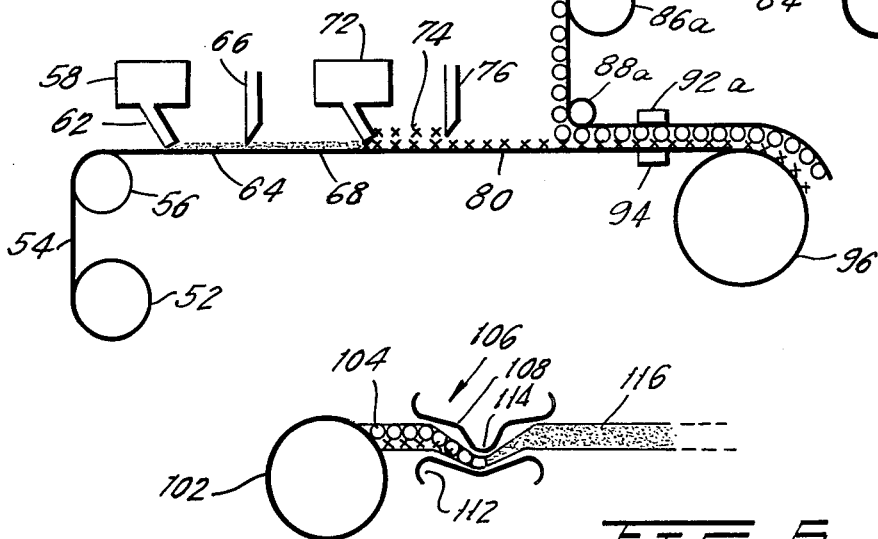
FIG. 5.
FIG. 6.

FOAM-FILLABLE ENCLOSURE

BACKGROUND OF THE INVENTION

1. Field of the Invention

The present invention relates to a hollow, enclosed unit, which may be in the form of a tape, sheet, or the like, which contains foam forming foam agents for being activated to form foam in the enclosure. The enclosed unit may be used in medical applications, as a splint or cast, in industrial applications, for insulating or blanketing purposes, and in numerous other applications where foamed material is desired.

2. Description of the Prior Art

Use of hardenable foam in an enclosure is known. See U.S. Pat. Nos. 3,563,234 and 3,048,169. The invention is concerned with generating the foam within that enclosure.

The present invention is an improvement upon the disclosure appearing in French Publication No. 2,267,082 which was published Nov. 7, 1975. That disclosure concerns a hollow, enclosed tubular tape, comprised of a top and a bottom layer which are edge sealed together to define a flat tape. The enclosure in the tubular tape contains two foam forming agents, one of which is microencapsulated to avoid its reacting with the other agent. The two agents are described as being mixed together, without disclosure as to how they are distributed. Upon activation of the foam forming agents, e.g. by application of pressure externally of the tape to break the microcapsules, the foam forming agents react and form foam in the tube.

The French publication lacks disclosure of appropriate foam forming agents and does not describe an effective manner of supporting both foam forming agents for generating a uniform consistency foam throughout the enclosure of the tubular tape and for precisely controlling the thickness of the foam across the enclosure.

Other characteristics of a foam filled enclosed unit are disclosed in the prior French publication, including various techniques of securing the layers of the enclosed unit together, of defining seals or obstructions at spaced intervals over the unit for helping to confine and prevent shifting of the foam forming agents and of the foam. The heights of these obstructions help define the height or thickness of the foam filled enclosure after the foam is formed.

The present invention is dependent upon effective microencapsulation of at least one of the active ingredients used in forming the foam. Now, microcapsules of liquid materials, such as water, encapsulated in an enclosure material, such as wax, can be distributed over a supporting surface in a uniform manner. See U.S. Pat. No. 3,423,489. Encapsulation technology of the last few years now makes possible the precise controlled distribution of foam forming materials across an entire enclosure.

Use of the invention for forming a splint or cast on a patient's limb is one possibility.

In the usual method of forming a cast or splint about a limb of a patient's body, plaster of Paris-impregnated or coated gauze ribbon is treated with water just prior to application to activate the plaster of Paris for subsequent setting, and then the wet, unset ribbon is wound about the affected limb. Both this method of forming a splint and cast, and the cast itself, have a number of disadvantages, which the present invention is intended to avoid. The step of wetting the gauze ribbon and the gauze ribbon produced are messy and inconvenient to the person wetting the gauze ribbon, the person using the gauze ribbon and the patient to whom it is applied. The setting of wetted plaster of Paris generates considerable heat which can be disturbing to the patient. Also, a plaster of Paris cast or splint is quite heavy. Its removal can be messy and cumbersome. Although newer plastic, fiberglass, or the like splints and casts are lighter in weight and avoid some of the above-described drawbacks, nonetheless, they are still not as light in weight nor as easily applied or removed as a foam-filled enclosure wrapped around the affected limb.

Mixing of an encapsulated substance with another within an enclosure, in a splint or cast forming context, is known, for example, from U.S. Pat. Nos. 3,415,243; 4,060,075; and 4,272,898. But the support and distribution of foam forming agents of the present invention are not disclosed.

Use of the invention for insulating, e.g. a building wall or other enclosed space, is another possibility.

Insulating a structure typically is done with either a viscous liquid foam material which is pumped into a space which is to receive insulation and sets and hardens in place or it is done with thick sheets of preformed insulating material that are applied on the walls or covering around the space. The viscous liquid foam material settles and compresses over time reducing the insulation protection and foam is often comprised of unprotected uncovered material which emits toxic fumes, like formaldehyde. Thick sheet insulation is heavy in weight, and its volume causes it to occupy a large storage space before it is used.

SUMMARY OF THE INVENTION

It is the primary object of the present invention to provide an enclosed unit generally in the form of a tape, sheet, or the like with a covering formed of flexible material which encases in the enclosure two separate materials, which will coact to form foam inside the enclosure and which are coacted to form the foam subsequent to the initial formation of the enclosed unit and usually when the unit is about to be applied.

It is another object of the invention to provide such enclosed unit, wherein the separate materials may be prevented from reacting to form foam until desired.

Another object of the invention is to precisely control the distribution of the foam generated in the enclosure.

Other objects and features of the invention will become apparent from the following general and subsequent more detailed description thereof.

The present invention provides an enclosed unit for containing foam forming material and for containing the foam that is generated. The enclosure of the unit is surrounded by an exterior covering layer that is preferably comprised of a flexible thermoplastic material. The material of the covering layer is not limited to plastic, so long as the material has the desired flexibility, is nonstretchable, can contain the foam and will give the foam filled unit a predetermined undistorted shape. The unit has any desired shape, such as an elongate tape, a sheet, or the like. Inside the exterior covering layer are provided the at least two chemically reactive agents, which react to form foam within the enclosure. These chemical agents are adapted to be activated a long time after fabrication of the enclosed unit and just prior to application of the unit, e.g. just prior to wrapping the unit around the affected limb of a body or just before applying the unit as insulation.

It is necessary to prevent premature reaction between the chemical agents. The above-noted French publication describes encapsulating at least one of the foam forming agents, which is in liquid form, in a non-reactive material, which protects the encapsulated agent from contacting and thereby reacting with the other agent, until the capsules are ruptured.

The French publication merely indicates the presence of two chemical agents in the enclosure, without describing any technique for mixing them or for supporting them in position in that enclosure to enable precise disposition of the agents for controlling foam distribution throughout the enclosure. Improvements in microencapsulation techniques, as shown in U.S. Pat. No. 3,423,489, for example, now enable better distribution of foam forming materials.

According to the invention, one foam forming agent, for example, toluene di-isocyanate (TDI) crystals, which foam when exposed to water, are coated on one surface inside the enclosure, and another encapsulated reagent, particularly microcapsules of an appropriate liquid reagent, for example, water, are coated on a second surface in the enclosure which is adjacent to and opposed to the one surface. The quantity and distribution of each chemical agent coated on its respective surface can be controlled with great precision.

More broadly described, the second agent on the second surface is so covered that it does not contact or mix with the first agent until a particular treatment of the unit designed to open or uncover the covered, protected agent and expose it to mix with the first agent.

The microcapsules of at least one of the agents can be broken by application of pressure or, as appropriate, by application of heat or exposure to radio frequency or microwave radiation which melts the protective layer of the microcapsules, or they can be opened by other techniques. The just released liquid agent will mix with the other chemical agent, e.g. the TDI crystals, to form foam in a desired pattern across the enclosure.

In its simplest form, one of the agents for forming foam in the enclosure is coated along one interior surface of the covering layer surrounding the enclosure and the other agent for forming the foam is coated on the opposite interior surface of the covering layer, so that when the opposite interior surfaces are squeezed together, this ruptures the microcapsules and initiates the reaction between the foam forming agents.

Coating each opposite surface with one of the foam forming agents has the benefit that the densities of both the foam forming agent and the microcapsules on their respective surfaces can be closely controlled, by doctoring, for instance, for generating the desired amount of foam in the enclosure. Furthermore, it is desirable that all of at least one of the foam forming agents, such as TDI crystals, be reacted with the other agent, such as water, for producing a predictable volume and distribution of foam. The invention permits the coatings of foam forming agents to be thin enough that all of at least one of the agents will be reacted with the other.

In a modification of the foregoing arrangement, the enclosed unit includes not only the top and bottom opposite covering layers, but there is also extending through and across the enclosure an additional layer between the exterior covering layers. In this embodiment, for example, the additional layer may be coated on both of its opposite surfaces with the non-encapsulated agent, e.g. TDI crystals, and the interior surfaces of both the top and bottom exterior, covering layers are coated with the encapsulated agent, e.g. microcapsules of water. Because the two layers carrying microcapsules are at the top and bottom exterior layers, the microcapsules can be readily broken by pressure, heat, radiation, etc. When the exterior layers are pressed together against the additional layer between them, foam is generated in the enclosures at both sides of the additional layer.

The additional layer effectively divides the enclosed unit into two enclosures, which causes two foam layers to be created. This is useful for a number of reasons. To assure that there is complete reaction between the two foam forming agents, the coatings of both of these materials on their respective surfaces in the enclosure are relatively thin. This helps assure that when the microcapsules are ruptured, there is complete mixing of the agents on both surfaces of the enclosure. However, the quantities of both crystalline material and of liquid held in microcapsules and coated on their surfaces is relatively small. As a result, the quantity of foam generated in any region of the enclosure might be less than desired. An enclosed unit with a double chamber enclosure is doubly thick when the foam is formed. It is apparent that while a single additional layer coated with foam forming agents on opposite surfaces might be provided, it is possible to have a second additional layer, or perhaps even more layers, in the enclosure, which would enable the enclosed unit to be controllably even thicker. With a plurality of additional layers, some of the microcapsules of liquid, or the like, would likely then be deeper inside the enclosure and might not be readily activated by pressure or heat applied at the exterior covering layer. However, the microcapsules could easily be ruptured by other means, such as radiation.

Foam forming TDI crystals are poisonous if ingested. The use of an enclosed unit permits possibly toxic foam forming materials to be used in the unit. Similarly, if the enclosed unit is used for insulating purposes and it were desired to use asbestos for additional fireproofing, shredded asbestos may be mixed with one foam forming material, e.g. TDI crystals, and when the foam is formed in the enclosure, the foam will perform a heat insulating and fireproofing function.

The individual exterior layers of the enclosure may be secured together at appropriate intervals for defining the extent to which the enclosed unit may expand as the foam is formed, thereby giving final shape to the enclosed unit. This will also minimize shifting of the foam across the enclosure before the foam has set firmly. The enclosed unit may have the form of a tube, tape, sheet or may be given any desired configuration, so long as it is enclosed for retaining the foam within the enclosure.

In a surgical application where the enclosed unit is applied to a part of the body, the unit may have holes punched in it or formed in it by appropriate sealing and punching during formation and by appropriate disposition of the coatings of foam forming materials so that the enclosed unit has openings or pores permitting ventilation.

An enclosed unit according to the invention may be fabricated in a number of ways. The interior surfaces of an upper and lower layer of an enclosed unit are coated with respective coatings of a foam forming agent. In one preferred technique of fabrication, for coating the interior surfaces of both the top and bottom layers of the unit with different respective foam forming agents, the unit is formed of two initially separate elongate sheets or webs which are later bonded together. Prior to assembly of the sheets together, the interior surface of one sheet layer is coated with one foam forming agent, e.g. TDI crystals, and the interior surface of the other sheet layer is coated with the other foam forming agent, e.g. microcapsules of water. These coatings are doctored on their surfaces to desired thicknesses for the amount of foam to be generated there. Thereafter, the layers are sealed together along their edges and at various spaced locations across their surfaces for completing and sealing the enclosure.

In a simple modification of the foregoing, an additional layer or layers to be disposed between the two outer layers is coated on both of its opposite surfaces with the respective foam forming agent which cooperates with the foam forming agent on the adjacent opposed surface when the enclosed unit is eventually assembled. The additional layer is then disposed between the two outer layers and the entire multilayer unit is sealed to define the multi-enclosure unit.

Other features of the invention will become apparent from the following description of the preferred embodiments of the invention considered in conjunction with the accompanying drawings.

BRIEF DESCRIPTION OF THE DRAWINGS

FIG. 1 is a perspective view of a foam forming and containment enclosed unit in the form of a tape, showing a first embodiment of the invention;

FIG. 2 is a plan view thereof with one of the layers partially broken away;

FIG. 3 is a side cross-sectional view thereof along the line 3—3 of FIG. 1;

FIG. 4 is the same type of view of an alternate embodiment thereof;

FIG. 5 is a schematic elevational view of an apparatus for forming the foam forming and containment enclosed unit according to the invention; and FIG. 6 is an elevational cross-sectional view of one form of apparatus for activating the foam forming and containment unit for producing foam within the enclosure.

DETAILED DESCRIPTION OF THE INVENTION

In the following, an enclosed unit in the form of a tubular tape is described. Other configurations are apparent.

Various foam generating chemical agents may be used in the enclosure of the invention. For illustrative purposes only, one foam forming agent comprises crystals of toluene di-isocyanate (TDI), which form foam in an exothermic reaction with another foam forming agent, water. To keep the water separate from the TDI crystals until foam is to be generated, the water is conventionally microencapsulated in microcapsules, or even in larger macrocapsules, but in any event in capsules of a material which does not react with TDI crystals, e.g. wax. See, for example, U.S. Pat. No. 3,423,489.

In its simplest form, the enclosed tubular tape is comprised of two exterior layers 12 and 14. The layers are of a flexible, non-stretchable, heat sealable, air and liquid impervious, thermoplastic, sheet material, such as polyethylene or polyvinylchloride. The layers, however, may be of any other flexible material, such as a paper product or metal foil, as appropriate, so long as they can contain the foam forming agents and the foam ultimately formed and do not stretch undesirably.

The upper layer 12 and the lower layer 14 are edge sealed together along their opposite continuous side marginal edges 16, 18. The layers are attached at 16 and 18 by heat sealing, by means of an appropriate solvent or adhesive or in any other manner known in the art. The technique, discussed below, for applying the foam forming agents to the respective layers enables the marginal edges 16, 18 of both layers to be free of these agents, enabling them to be sealed together.

The inwardly facing undersurface of the top layer 12 has adhered thereto a coating 20 of TDI crystals which extends across that entire undersurface. The inwardly facing opposite top surface of the bottom layer 14 carries a coating 22 of wax coated microcapsules of water placed so that the coatings 20, 22 are overlaid. The thicknesses of the coatings 20 and 22 are selected so that when the microcapsules in coating 22 are eventually ruptured, the released water will completely mix with all of the crystals in the coating 20 for forming a predictable quantity and therefore predictable thickness layer of foam in the enclosure between the layers 12 and 14.

The foam layer generated in the enclosure between the top and bottom layers 12 and 14 may not be sufficiently thick or tall for a particular application. The thickness of the foam layer is determined by the thickness of the coatings 20, 22 and these are limited for assuring that there will be complete mixing of the water from the microcapsules and the TDI crystals for forming a predictable thickness foam layer.

For producing a thicker foam-filled enclosed unit, another embodiment, shown in FIG. 4, is contemplated, wherein there are the exterior top and bottom layers 26, 28, as in the first embodiment, and there is an additional intermediate layer of the same or the like plastic material 30 disposed between the top and bottom layers 26 and 28. The three layers 26, 28 and 30 are sealed along their edge margins as at 16 and 18 in the first embodiment. Effectively, there are two foam enclosures in this one enclosed unit, between the top and intermediate layers 26 and 30 and between the intermediate and bottom layers 30 and 28. The interior surfaces of both the top and bottom layers 26 and 28 are coated with respective coatings 32 and 34 of microcapsules of water. Both opposite surfaces of the intermediate layer 30 are coated with respective coatings 36, 38 of TDI crystals. When the coatings of microcapsules 32, 34 are ruptured, the water released mixes with the TDI crystals in the coatings 36, 38 and generates foam in the enclosures both above and below the intermediate layer 30. This two foam-filled enclosure thick unit is thicker than the foam-filled enclosure of the first embodiment, assuming that the microcapsule coating and the TDI crystal coating in both cases have the same characteristics.

The rupturable microcapsule coatings 32, 34 are disposed on the exterior layers 26, 28 to be more accessible to rupturing means, such as a mechanical rupturing means, or one which applies heat or radiation. The microcapsules may alternately be at the intermediate layer 30, as appropriate, and still be ruptured by mechanical force, by heat, by other electromagnetic radiation, etc.

Yet more intermediate layers, such as layer 30, may be provided inside the enclosure, one layer above the other.

Referring to FIG. 2, the layers 12 and 14 may be held together not only at the edge margins 16 and 18, but at spaced locations across the enclosure. For this purpose, the bottom layer 14 may be provided with upstanding deposits or projections 42 of plastic material or may be initially formed with the upstanding projections 42 at spaced locations across the layer. When the layers 12 and 14 are sealed together, the sealing also occurs between the tops of the projections 42 and the underside of the upper layer 12. The projections 42 and their attachment to the opposite outer layer of the strip can serve a number of functions. They prevent gathering, bunching or clumping of the chemical agents in one region of the enclosure. Of course, coating these agents on the interior surfaces in the enclosure also serves this function. The projections serve as baffles preventing movement of foam forming agents, if that might occur, and preventing movement of generated foam. The distances of the projections from each other controls the maximum degree of expansion of the foam and thus also helps to control the density of the foam and thereby also controls the rigidity of the resulting enclosed unit. Further, the connections prevent shifting of the layers 12 and 14 with respect to each other, both before and after foam is generated. Further, when the foam is formed, the projections 42 will limit the extent of inflation of the enclosure, and will ensure the desired degree of uniformity of inflation of the enclosure, giving the entire enclosed unit the desired height, or it will enable different height sections of the unit to develop, as desired. Also, in holding the layers apart, the projections 42 may prevent premature rupture of the microcapsules by inadvertent pressure upon them or from the normal pressure upon the enclosed unit while it is held in storage prior to use.

Furthermore, at spaced locations along the enclosed unit, openings 46 may be defined through both of the layers 12 and 14, e.g. for fastening the unit to an object or surface (as with sheets of insulation) or for permitting air ventilation (as with a tape wrapped about a person's limb). The margin of the opening 46 would be sealed closed, as with the sealing together of the layers 12 and 14 at the margins 16 and 18. The foam forming agents would be absent from the inward surfaces of the layers 12 and 14 in the vicinity of the openings 46 to permit the layers to be attached together at the margins of the openings.

FIG. 5 schematically illustrates a method of fabricating and an apparatus for fabricating an enclosed unit according to the invention.

A supply roll 52 supplies an elongate strip 54 of flexible plastic material. The strip moves beneath the adhesive supply means 58 to which adhesive material is delivered through the chute 62, forming the thick adhesive coating 64 on the strip 54. The adhesive material must be one which does not react with TDI crystals that are to be held by the adhesive to the strip 54. The adhesive coating is precisely doctored to a desired thickness by the doctor blade 66. In addition, by various means, the adhesive may be entirely removed at certain locations, e.g. at the openings 46, described above. Means for forming such an opening, e.g. a punch, are not shown. The strip 54 next moves beneath the hopper 72 which delivers a continuous supply of TDI crystals in a too thick coating 74 which must be doctored to the desired height. The doctor blade 76 strips away excess TDI crystals, providing a precisely thick coating 80 of the crystals, which will produce a predetermined quantity of foam in the completed enclosure. When the adhesive sets, it holds the crystals securely.

The schematic FIG. 5 suggests simultaneous formation of the initially separate layer carrying the microcapsules of water. However, that layer may be initially formed remotely, both in space and in time, from the layer carrying TDI crystals, and the two layers may be brought together for formation into the enclosed unit for the first time just before such unit is formed.

A supply roll 82 also supplies an elongate second strip 84 of flexible plastic material to which a coating of microcapsules of water for reacting with TDI crystals are applied. A microcapsule producing apparatus 86, which may be of the type shown in U.S. Pat. No. 3,423,489, supplies microcapsules of water through its supply tube 88, and the microcapsules 90 form a coating 92 on the strip 84 which coating will have the desired thickness and distribution, dependent upon the quantity of microcapsules generated during any period of time and the velocity of the strip 84. Additionally, an appropriate doctor means (not shown) may also control the thickness of the microcapsule coating. Although the microcapsules are shown as individual visible units, in fact they are quite small, and may not be individually visible to the unaided eye. Alternatively, macrocapsules of liquid may be used, defining individual beads of water. The size of the capsules is not so significant, so long as a sufficient quantity of water will be supplied for reacting with the TDI crystals when the capsules are ruptured. Following their initial formation, the capsules themselves may be sufficiently tacky to adhere to strip 84, without additional adhesive, if they are applied shortly after they are formed. Alternatively, additional adhesive may be applied to the strip 84, as at means 58 for the TDI crystals, and this will hold the capsules to the strip 84.

The microcapsule coated surface of the strip 84 is redirected by rolls 86a, 88a to overlie, without pressing against, the TDI crystal coated surface of the strip 54 and during the now parallel, overlying run of the strips, heat seal means 92a seal the margins of the strip and may heat seal one layer to posts 42, if the posts are present. This forms the previously separate strips 54, 84 into a closed tube.

This tube is loosely wound around the take-up roll 94. It is not wound too tightly, as too great pressure might rupture the microcapsules. Now, a tubular tape enclosure containing unreacted foam forming agents has been formed.

FIG. 6 schematically shows one manner in which an enclosed unit according to the invention is activated. The roll 102 carries the preformed strip form enclosed unit 104 having two opposite layers supporting coatings of foam forming material in an enclosure. The strip is unwound past the activating mechanism which comprises two plates 108, 112 on opposite sides of the strip 104. The plate 108 has a sharp edge due to a change of direction 114 and the strip 104 is sharply bent there and is pressed against the edge 114. As the strip 104 is drawn out between the plates 108, 112, the layer thereof carrying the microcapsules of liquid is pressed against the edge 114, which breaks the microcapsules, so that they can mix with the TDI crystals and form the foam layer 116 inside the exterior layers. The chemical reaction between the TDI and the water causes production of an expanded foam layer 116. The exterior layers are sufficiently stretchable to allow considerable expansion in the volume of the foam. The foam-filled enclosed unit is placed where desired, and the foam sets and hardens.

Although the present invention has been described in connection with a number of preferred embodiments thereof, many variations and modifications will now become apparent to those skilled in the art. It is preferred therefore, that the present invention be limited not by the specific disclosure herein, but only by the appended claims.

What is claimed is:

1. An enclosed unit for defining an enclosure for generation and containment of foam therein, comprising;
    a first and a second layer of flexible material for containing generated foam and foam forming agents; the first and second layers being joined together for defining an enclosure between them; the first and second layers having respective first and second opposite surfaces which face toward each other and into the enclosure;
    a first foam forming agent coated on and supported on the first surface; a second foam forming agent coated on and supported on the second surface; the first and second agents being such that upon mixing together of the agents, they generate foam in the enclosure between the first and second surfaces;
    at least one of the foam forming agents being encapsulated in rupturable capsules comprised of a material which contains the agent, the capsules being for preventing mixing of the first and second agents, the capsules being adapted to be ruptured for releasing the agent encapsulated, whereby upon capsule rupture the agents come into contact and coact to generate foam in the enclosure.

2. The unit of claim 1, wherein the layers are comprised of a thermoplastic material.

3. The unit of claim 1, wherein at least one of the first and second layers is at the exterior of the unit.

4. The unit of claim 3, wherein both of the first and second layers are at the exterior of the unit at opposite sides of the unit.

5. The unit of claim 4, wherein the unit comprises at least one additional layer between the exterior layers; the additional layer having a third surface facing and being opposite one of the first and second surfaces and a foam-forming agent being coated on the third surface and that agent being selected to generate foam when mixed with the agent on the respective one of the first and second surfaces to which the third surface faces; whereby an enclosure is defined between the third surface and the surfaces it faces.

6. The unit of claim 5, wherein the additional layer has a respective one of the third surfaces at both of its opposite surfaces, whereby a respective enclosure is defined above both opposite surfaces of the additional layer.

7. The unit of claim 1, wherein the layers are overlaid and have respective marginal edges which are secured together for defining the edges of the enclosure and for enclosing the enclosure.

8. The unit of claim 7, wherein the layers are comprised of a thermoplastic material.

9. The unit of claim 1, wherein the layers are comprised of a non-stretchable material.

10. The unit of claim 9, wherein the layers are comprised of a thermoplastic material.

11. The unit of claim 1, further comprising a plurality of posts in the enclosure and extending between the opposite first and second surfaces for spacing apart those opposite surfaces.

12. The unit of claim 11, wherein the posts are defined in one of the first and second surfaces and are attached to the other of the first and second surfaces.

13. The unit of claim 1, wherein one of the agents comprises crystals of toluene di-isocyanate and the other agent comprises water in capsules, the capsules being of a material which does not react with toluene di-isocyanate.

14. An enclosed unit for defining an enclosure for generation and containment of foam therein, comprising;
    a first and a second layer of flexible material for containing generated foam and foam forming agents; the first and second layers being formed together for defining an enclosure between them; the first and second layers having respective first and second opposite surfaces which face toward each other and into the enclosure;
    a first foam forming agent coated on and supported on the first surface; a second foam forming agent coated on and supported on the second surface; the first and second agents being such that upon mixing together of the agents, they generate foam in the enclosure between the first and second surfaces;
    at least one of the agents being supported on its respective surface with means which prevent mixing of the one agent with the other agent, and that means being adapted for being operated upon to release the one agent to mix with the other agent, whereby upon such operation upon that means, the agents come into contact and coact to generate foam in the enclosure.

15. A method of forming a unit to define an enclosure for generation and containment of foam therein, the method comprising:
    coating a first foaming agent on one inwardly facing surface of a first layer comprised of a flexible material which defines the enclosure;
    coating a second foam-forming agent on a second inwardly facing surface of a second layer of a flexible material which defines the enclosure, wherein the first and second surfaces face each other and are opposite each other;
    wherein at least one of the agents is encapsulated in rupturable capsules comprised of a material which contains the one agent and which material does not react with the other agent, and the capsules are for preventing mixing of the first and second agents, the capsules being adapted to be ruptured for releasing the agent encapsulated, whereby upon capsule rupture, the agents come into contact and react to generate foam in the enclosure.

16. The method of claim 15, wherein the first and second layers are initially separate and their coated surfaces are respectively coated while the layers are separate; after coating of the first and second surfaces of the layers, securing the layers together with the coated surfaces facing each other opposite each other and overlaid.

17. The method of claim 15, wherein the agents are coated on their respective surfaces by adhering them to those surfaces.

18. The method of claim 15, including a third one of the layers located outside the second agent and the foam-filled enclosure is defined between the first and second layers.

19. The method of claim 18, further comprising coating the third surface of the second layer on the opposite side of the second layer, with one of the first and second agents and coating the inwardly facing fourth surface of the third layer, which is opposite and faces toward the third layer, with the other of the first and second agents.

20. A method for producing a foam-filled enclosure, comprising forming the unit according to claim 15, and thereafter rupturing the capsules for freeing the one agent to contact the other agent for generating foam in the enclosure.

* * * * *